(12) United States Patent
Fu et al.

(10) Patent No.: US 11,849,914 B2
(45) Date of Patent: Dec. 26, 2023

(54) ENDOSCOPIC IMAGE PROCESSING METHOD AND SYSTEM, AND COMPUTER DEVICE

(71) Applicant: TENCENT TECHNOLOGY (SHENZHEN) COMPANY LIMITED, Guangdong (CN)

(72) Inventors: Xinghui Fu, Shenzhen (CN); Zhongqian Sun, Shenzhen (CN); Wei Yang, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 638 days.

(21) Appl. No.: 17/078,826

(22) Filed: Oct. 23, 2020

(65) Prior Publication Data

US 2021/0052135 A1 Feb. 25, 2021

Related U.S. Application Data

(63) Continuation of application No. PCT/CN2019/112202, filed on Oct. 21, 2019.

(30) Foreign Application Priority Data

Oct. 30, 2018 (CN) .......................... 201811276885.2

(51) Int. Cl.
*A61B 1/00* (2006.01)
*G06N 3/045* (2023.01)

(52) U.S. Cl.
CPC ...... *A61B 1/0005* (2013.01); *A61B 1/000094* (2022.02); *A61B 1/000096* (2022.02); *G06N 3/045* (2023.01)

(58) Field of Classification Search
CPC ............ A61B 1/0005; A61B 1/000094; A61B 1/000096; G06N 3/045; G06N 3/084;
(Continued)

(56) References Cited

U.S. PATENT DOCUMENTS 6,292,791 B1 * 9/2001 Su .......................... G10H 7/00
706/15
2018/0225820 A1 8/2018 Liang et al.
(Continued)

FOREIGN PATENT DOCUMENTS

CN 106022221 10/2016
CN 106097340 11/2016
(Continued)

OTHER PUBLICATIONS

International Preliminary Report on Patentability Chapter I from the Chinese Paten Office dated May 4, 2021 (Year: 2021).*
(Continued)

*Primary Examiner* — Juan A Torres
(74) *Attorney, Agent, or Firm* — ARENTFOX SCHIFF LLP (57) ABSTRACT

An endoscopic image processing method is provided. The method can include acquiring a current endoscopic image of a to-be-examined user, and predicting the current endoscopic image by using a deep convolutional network based on a training parameter. The training parameter can be determined according to at least one first endoscopic image and at least one second endoscopic image transformed from the at least one first endoscopic image, where the at least one endoscopic image corresponds to a human body part. The method can further include determining an organ category corresponding to the current endoscopic image. The method (Continued)

can make a prediction process more intelligent and more robust, thereby improving resource utilization of a processing apparatus.

18 Claims, 5 Drawing Sheets

(58) Field of Classification Search
CPC ......... G06T 7/0012; G06T 2207/10068; G06T 2207/20081; G06T 2207/30004
USPC ....................................................... 382/128
See application file for complete search history.

(56) References Cited

U.S. PATENT DOCUMENTS

| | | | |
|---|---|---|---|
| 2018/0225828 A1 | 8/2018 | Guo et al. | |
| 2018/0247107 A1 | 8/2018 | Murthy et al. | |
| 2019/0005377 A1* | 1/2019 | Malaya | G06N 3/042 |
| 2019/0034800 A1 | 1/2019 | Shiratani | |
| 2020/0097742 A1* | 3/2020 | Ratnesh Kumar | G06V 20/52 |
| 2020/0143248 A1* | 5/2020 | Liu | G06N 3/08 |

FOREIGN PATENT DOCUMENTS

| | | |
|---|---|---|
| CN | 107730489 | 2/2018 |
| CN | 108615037 | 10/2018 |
| CN | 109523522 | 3/2019 |
| JP | 2017-45341 A | 3/2017 |
| WO | WO 2017175282 | 10/2017 |
| WO | WO 2017193906 | 11/2017 |
| WO | WO 2018/008593 A1 | 11/2018 |
| WO | WO 2018/225448 A1 | 12/2018 |

OTHER PUBLICATIONS

Claims filed after receipt of (European) search report dated May 30, 2022 (Year: 2022).*
International Search Report dated Jan. 21, 2020 in International Application No. PCT/CN2019/112202, (5 pages).
Written Opinion dated Jan. 21, 2020 in International Application No. PCT/CN2019/112202. (4 pages).
Extended European Search Report issued in Application No. 19879131.1 dated Nov. 30, 2021 (6 pages).
Office Action issued in Japanese Patent Application No. 2020-560333 dated Nov. 22, 2021 (with English translation of Office Action summary) (6 pages).

* cited by examiner

ENDOSCOPIC IMAGE PROCESSING METHOD AND SYSTEM, AND COMPUTER DEVICE

RELATED APPLICATION

This application is a continuation of International Application No. PCT/CN2019/112202, filed on Oct. 21, 2019, which claims priority to Chinese Patent Application No. 201811276885.2, entitled "ENDOSCOPIC IMAGE PROCESSING METHOD, APPARATUS AND SYSTEM, AND STORAGE MEDIUM" and filed on Oct. 30, 2018. The entire disclosures of the prior applications are hereby incorporated by reference in their entirety.

FIELD OF THE TECHNOLOGY

The present disclosure relates to the field of image processing technologies, including to an endoscopic image processing method and system, and a computer device.

BACKGROUND OF THE DISCLOSURE

At present, stomach cancer and esophagus cancer are among the top five malignant tumor types that occur frequently in China and around the world. Both stomach cancer and esophagus cancer are malignant tumors occurring in an upper gastrointestinal tract. In actual clinical practice, a doctor conducts an electronic examination by using an endoscope. The endoscope enters the upper gastrointestinal tract from the mouth of a patient. Strong light is emitted from a light source and an optical fiber allows the light to make a turn, so that the doctor can observe the health status of various organs in the upper gastrointestinal tract.

However, when medical images are shot by an endoscope, due to different acquisition environments, detection devices and shooting habits of doctors, endoscopic images of the same organ differ greatly in visual performance. Local manifestations of different organs may be very similar, therefore seriously affecting disease diagnose of a doctor.

In order to identify different organs in medical images, a computer vision technology is usually used for extracting features such as a color, a texture, a gradient, and local binary patterns (LBP), and then organs are classified and identified by using a support vector machine (SVM) classification method. However, such a technology requires researchers to have a deep understanding of medical images, in order to make a feasible feature extraction solution according to inherent characteristics of the images. In addition, the extracted features tend to be general features, rather than specific organ features extracted purposefully for a to-be-diagnosed body part. As a result, the coverage is incomplete and the solution is not robust enough.

SUMMARY

Embodiments of the present disclosure provide an endoscopic image processing method and system, and a computer device, to make a prediction process more intelligent and more robust, thereby improving resource utilization of a processing apparatus.

Aspects of the present disclosure provide an endoscopic image processing method. The method can include acquiring a current endoscopic image of a to-be-examined user, and predicting the current endoscopic image by using a deep convolutional network based on a training parameter, the training parameter being determined according to at least one first endoscopic image and at least one second endoscopic image transformed from the at least one first endoscopic image, the at least one first endoscopic image corresponding to a human body part. The method can further include determining an organ category corresponding to the current endoscopic image.

The present disclosure further provides an endoscopic image processing system that can include a human body detection device and an endoscopic image processing apparatus. The human body detection device can be configured to detect a human body part and transmit at least one detected first endoscopic image to the endoscopic image processing apparatus. The endoscopic image processing apparatus can be configured to acquire the at least one first endoscopic image from the human body detection device, create a deep convolutional network for endoscopic image prediction and determine a training parameter of the deep convolutional network according to the at least one first endoscopic image and at least one second endoscopic image transformed from the at least one first endoscopic image, and acquire a current endoscopic image of a to-be-examined user, predict the current endoscopic image by using the deep convolutional network and based on the training parameter, to determine an organ category corresponding to the current endoscopic image.

In addition, the present disclosure further provides a non-transitory computer readable storage medium that stores computer readable instructions that, when executed at by least one processor, cause the at least one processor to load and perform the operations including acquiring a current endoscopic image of a to-be-examined user, and predicting the current endoscopic image by using a deep convolutional network based on a training parameter. The training parameter being determined according to at least one first endoscopic image and at least one second endoscopic image transformed from the at least one first endoscopic image, and the at least one first endoscopic image corresponding to a human body part. The operations can further include determining an organ category corresponding to the current endoscopic image.

In addition, the present disclosure further provides a computer device, including at least one processor and at least one memory that stores at least one piece of program code that, when executed by the at least one processor, can implement operations including acquiring a current endoscopic image of a to-be-examined user, and predicting the current endoscopic image by using a deep convolutional network based on a training parameter. The training parameter can be determined according to at least one first endoscopic image and at least one second endoscopic image transformed from the at least one first endoscopic image, and the at least one first endoscopic image corresponding to a human body part. The operations can further include determining an organ category corresponding to the current endoscopic image.

It can be seen from the foregoing technical solutions that, according to the method provided in the embodiments of the present disclosure, a feature extraction process can be obtained completely by a model of a deep convolutional network through self-learning, while a researcher does not need to deeply understand a medical image, thus reducing the dependence on a professional level of a doctor, so that the whole prediction process is more intelligent. In addition, the amount of annotated data used in a training process can be reduced, thus improving a training convergence speed, providing clean available data for next disease diagnosis, providing available integration modules for disease diagnosis of different organs, and improving resource utilization of a processing apparatus.

BRIEF DESCRIPTION OF THE DRAWINGS

Further features, the nature, and various advantages of the disclosed subject matter will be more apparent from the following detailed description and the accompanying drawings of exemplary embodiments in which.

DESCRIPTION OF EMBODIMENTS

To make the objectives, technical solutions, and advantages of the present disclosure clearer and more comprehensible, the following further describes the present disclosure with reference to the accompanying drawings and exemplary embodiments.

Figure 1:
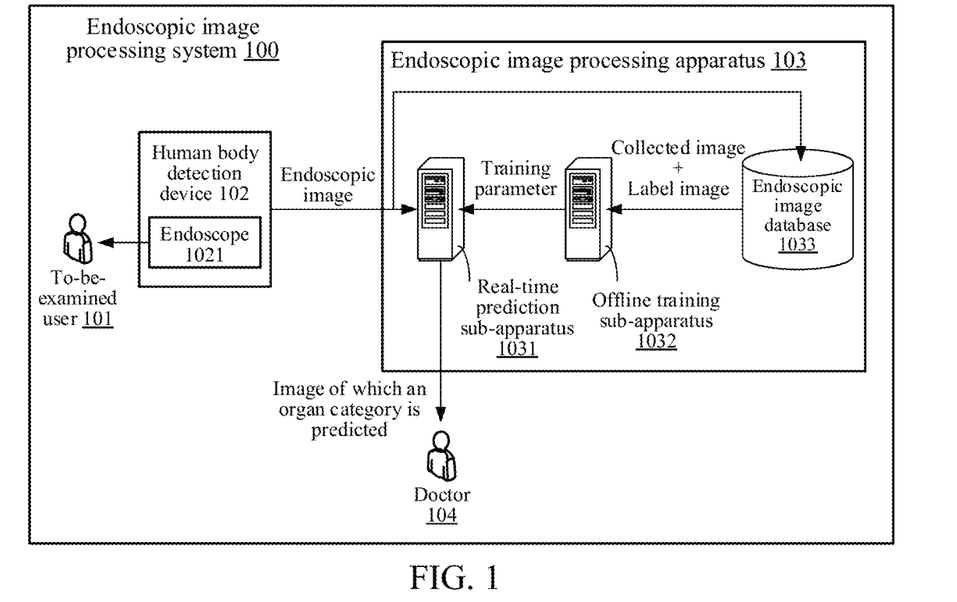
FIG. 1 is a schematic structural diagram of an endoscopic image processing system related to an embodiment of the present disclosure.

FIG. 1 is a schematic structural diagram of an endoscopic image processing system related to an embodiment of the present disclosure. As shown is FIG. 1, an endoscopic image processing system 100 includes a to-be-examined user 101, a human body detection device 102 including an endoscope 1021, an endoscopic image processing apparatus 103, and a doctor 104. The endoscopic image processing apparatus 103 may include a real-time prediction sub-apparatus 1031, an offline training sub-apparatus 1032, and an endoscopic image database 1033.

According to the embodiments of the present disclosure, the human body detection device 102 detects a human body part of the to-be-examined user 101 by using the endoscope 1021. The human body detection device 102 transmits a collected endoscopic image to the endoscopic image processing apparatus 103. Specifically, the collected endoscopic image may be transmitted to the real-time prediction sub-apparatus 1031 as a to-be-predicted current endoscopic image, or may be transmitted to the endoscopic image database 1033 for storage. Images stored in the endoscopic image database 1033 is used for performing offline training.

According to the embodiments of the present disclosure, when the doctor 104 intends to diagnose a disease based on the to-be-predicted current endoscopic image, the real-time prediction sub-apparatus 1031 first needs to obtain a training parameter from the offline training sub-apparatus 1032, and then predicts the current endoscopic image based on the training parameter and a created deep convolutional network, to determine an organ category corresponding to the current endoscopic image. For example, the organ category may be a duodenum in an upper gastrointestinal tract. In a process of generating the training parameter, the offline training sub-apparatus 1032 uses the deep convolutional network the same as that of the real-time prediction sub-apparatus 1031 to acquire an image collected through an endoscope and an annotated label image from the endoscopic image database 1033, and performs off-line training according to the image collected by the endoscope and the annotated label images, to output the training parameter of the deep convolutional network.

Herein, the foregoing human body detection device 102 refers to a medical terminal device equipped with the endoscope 1021 and having an image collection function. The endoscope 1021 may include an image sensor, an optical lens, a light source for illumination, a mechanical device and so on. The endoscopic image processing apparatus 103 may be a server or a cloud server with an image storage and processing function. All the terminal devices are installed with an operating system, including but not limited to an Android operating system, a Symbian operating system, a Windows mobile operating system, and an iPhone OS operating system. The human body detection device 102 and the endoscopic image processing apparatus 103 may communicate with each other through a wired or a wireless network.

Figure 2:
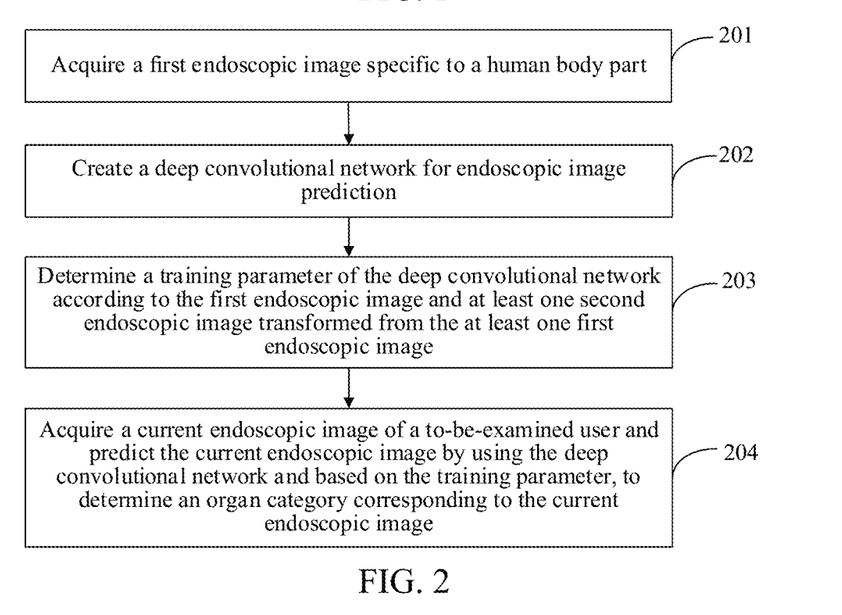
FIG. 2 is a schematic flowchart of an endoscopic image processing method according to an embodiment of the present disclosure.

FIG. 2 is a schematic flowchart of an endoscopic image processing method according to an embodiment of the present disclosure. The method is applied to a computer device. The computer device being a server is used as an example for description. This exemplary embodiment can include the following steps.

In step 201, the server acquires at least one first endoscopic image specific to a human body part. That is, the at least one first endoscopic image corresponds to the human body part.

In step 202, the server creates a deep convolutional network for endoscopic image prediction.

In step 203, the server determines a training parameter of the deep convolutional network according to the at least one first endoscopic image and at least one second endoscopic image transformed from the at least one first endoscopic image.

In step 204, the server acquires a current endoscopic image of a to-be-examined user and predicts the current endoscopic image by using the deep convolutional network and based on the training parameter, to determine an organ category corresponding to the current endoscopic image. In other words, the foregoing training parameter is determined according to the at least one first endoscopic image and the at least one second endoscopic image transformed from the at least one first endoscopic image.

Based on the embodiments, the foregoing steps are described below in detail.

In the foregoing step 201, the human body part may be detected by using a detection device including an endoscope, to obtain the at least one first endoscopic image. The human body part includes one or more organs. For example, the human body part is an upper gastrointestinal tract. The upper gastrointestinal tract includes five organs: a pharynx, an esophagus, a stomach, a cardia and a duodenum. The detection device may shoot a picture or a video, and the acquired first endoscopic image may be a white light RGB image.

Figure 3:
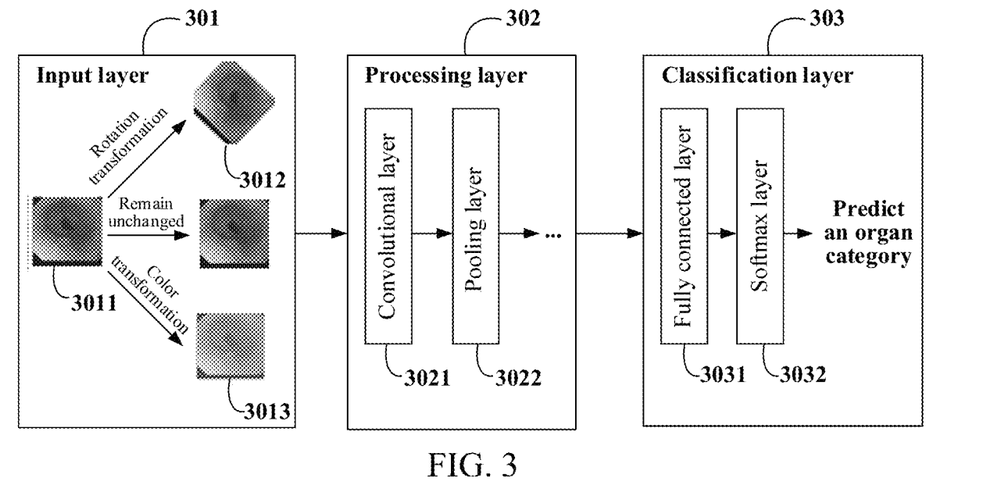
FIG. 3 is a schematic structural diagram of a deep convolutional network according to an embodiment of the present disclosure.

In the foregoing step 202, the deep convolutional network for classifying the endoscopic image is a convolutional neural network based on deep learning. Specifically, the deep convolutional network includes an input layer, a processing layer, and a classification layer. FIG. 3 is a schematic structural diagram of a deep convolutional network according to an embodiment of the present disclosure. As shown in FIG. 3, in the deep convolutional network, an input layer 301 determines at least one endoscopic image as an input. A processing layer 302 performs feature extraction on the inputted endoscopic images. A classification layer 303 outputs organ categories obtained by predicting the inputted endoscopic images. The foregoing at least one endoscopic image may include first endoscopic images shot by a detection device. Certainly, the at least one endoscopic image may further include second endoscopic images obtained by transforming the first endoscopic images, to increase a sample size.

In the processing layer 302, a convolutional layer 3021 performs feature extraction on the endoscopic image by using a convolution matrix as a filter, to obtain a feature image. A pooling layer 3022 is configured to simplify information outputted by the convolutional layer, to reduce data dimensions and computational overheads, and control over-fitting.

In a classification layer 303, a fully connected layer 3031 is configured to determine an organ category closest to the acquired feature image. A softmax layer 3032 outputs a 1×M-dimensional classification vector, the softmax layer being used for index normalization. M is the quantity of alternative organ categories. For example, there are six alternative organ categories: a non-organ map, a pharynx, an esophagus, a stomach, a cardia, and a duodenum. A value of an element in the classification vector is [0, 1], and an $i^{th}$ element represents a probability of the endoscopic image as an input belonging to an $i^{th}$ alternative organ category.

In an embodiment of the present disclosure, in a process of creating the deep convolutional network, a server may add at least one densely connected layer into the processing layer, the densely connected layer including a plurality of connected sub-layers. For each connected sub-layer, a feature outputted by other connected sub-layers before the connected sub-layer is used as an input of the connected sub-layer.

Figure 4:
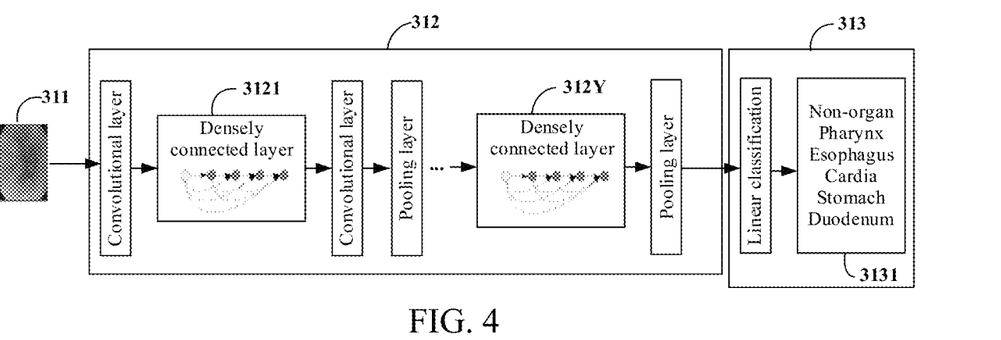
FIG. 4 is a schematic structural diagram of a deep convolutional network according to another embodiment of the present disclosure.

FIG. 4 is a schematic structural diagram of a deep convolutional network according to another embodiment of the present disclosure. As shown in FIG. 4, a processing layer 312 includes Y densely connected layer 3121 to 312Y. Each densely connected layer includes a plurality of connected sub-layers, as shown by solid circles in boxes 3121 to 312Y in FIG. 4. Probabilities of six categories as shown in a box 3131 are outputted in an output layer 313. An endoscopic image 311 may be input to the processing layer 312, for example.

Figure 5:
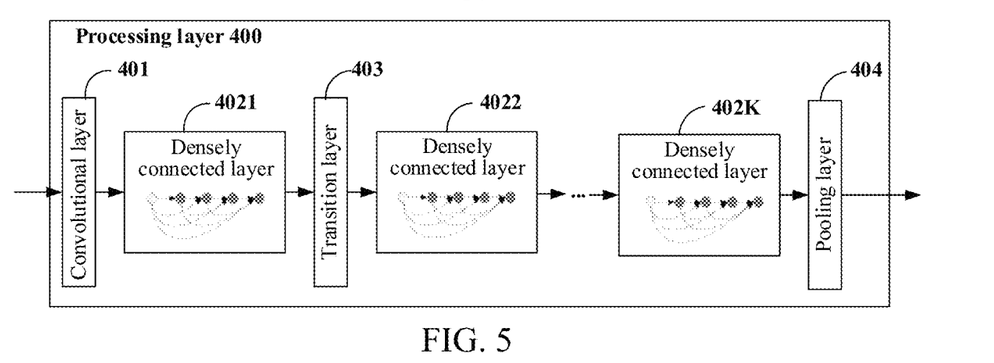
FIG. 5 is a schematic structural diagram of a processing layer according to still another embodiment of the present disclosure.

FIG. 5 is a schematic structural diagram of a processing layer according to still another embodiment of the present disclosure. As shown in FIG. 5, in a structure of a processing layer 400, there are K densely connected layers 4021 to 402K between a convolutional layer 401 and a pooling layer 404. In the same densely connected layer, a feature outputted by each connected sub-layer is inputted into subsequent other connected sub-layers.

It is assumed that the densely connected layer includes J connected sub-layers, and a processing function of a $j^{th}$ connected sub-layer is $H_j$, j=1 . . . , J. Then, a feature $z_j$ outputted by the $j^{th}$ connected sub-layer may be obtained through calculation according to the following formula:

$$z_j = H_j([z_0, z_1, \ldots, z_{j-1}]) \tag{1}$$

where $[z_0, z_1, \ldots, z_{j-1}]$ represents cascading the features outputted by the connected sub-layers with serial numbers 0 to j−1. $H_j$ may be an operation such as batch normalization (BN), ReLU activation and 3×3 convolution. In a case that the quantity of channels of the densely connected layer is $k_0$, then the quantity of channels of a $j^{th}$ layer is $k_0+(j-1)\times k$, k being a growth rate. With an increase in the quantity of the connected sub-layers, the quantity of channels increases linearly with k.

In an embodiment of the present disclosure, when at least one densely connected layer is added into the processing layer, in order to further compress parameters, a transition layer may further be added between two adjacent densely connected layers. As shown in FIG. 5, a transition layer 403 is added between a densely connected layer 4021 and a densely connected layer 4022. If there are K densely connected layers, the quantity of the transition layers is K−1. A feature compression ratio of the transition layer may be set according to a preset prediction precision. Since a compression ratio affects the quantity of parameters and the prediction precision, a value of the feature compression ratio is set according to the preset prediction precision specific to the endoscopic image. For example, the value is set to 0.5.

In another embodiment of the present disclosure, the server determines specific parameters of the processing layer and the classification layer in the deep convolutional network according to the quantity of to-be-predicted endoscopic images, the prediction precision and the adjustment of a hyper parameter in a training process. Table 1 is an example of a structure and parameters of a deep convolutional network including 4 densely connected layers and 3 transition layers. The growth rate of each densely connected layer may be set to 24; a 1×1 convolution operation may further be performed before the 3×3 convolution operation, thereby reducing the quantity of the input feature images and fusing features of the channels. The 1×1 convolution operation in the transition layer may reduce the quantity of the input channels by half

TABLE 1

Example of structure and parameters of deep convolutional network

| Sub-layers included in processing layer | Output dimensions | Parameters used by each sub-layer |
|---|---|---|
| Convolutional layer | 112 × 112 | 7 × 7 convolution, stride: 2 |
| Pooling layer | 56 × 56 | 3 × 3 max pooling, stride: 2 |
| Densely connected layer (1) | 56 × 56 | $\begin{bmatrix} 1\times1 \text{ Convolution} \\ 3\times3 \text{ Convolution} \end{bmatrix} \times 6$ |
| Transition layer (1) | 56 × 56 <br> 28 × 28 | 1 × 1 convolution <br> 2 × 2 average pooling, stride: 2 |
| Densely connected layer (2) | 28 × 28 | $\begin{bmatrix} 1\times1 \text{ Convolution} \\ 3\times3 \text{ Convolution} \end{bmatrix} \times 12$ |

TABLE 1-continued

Example of structure and parameters of deep convolutional network

| Sub-layers included in processing layer | Output dimensions | Parameters used by each sub-layer |
|---|---|---|
| Transition layer (2) | 28 × 28<br>14 × 14 | 1 × 1 convolution<br>2 × 2 average pooling, stride: 2 |
| Densely connected layer (3) | 14 × 14 | $\begin{bmatrix} 1 \times 1 \text{ Convolution} \\ 3 \times 3 \text{ Convolution} \end{bmatrix} \times 24$ |
| Transition layer (3) | 14 × 14<br>7 × 7 | 1 × 1 convolution<br>2 × 2 average pooling, stride: 2 |
| Densely connected layer (4) | 7 × 7 | $\begin{bmatrix} 1 \times 1 \text{ Convolution} \\ 3 \times 3 \text{ Convolution} \end{bmatrix} \times 16$ |
| Classification layer | 1 × 1 | 7 × 7 global average pooling<br>2D fully connected, softmax output |

In step 203, when training the deep convolutional network, the server may determine a training parameter of the deep convolutional network according to at least one first endoscopic image and at least one second endoscopic image transformed from the at least one first endoscopic image. Specifically, the server transforms the at least one first endoscopic image, to obtain at least one transformed second endoscopic image, and then inputs the at least one first endoscopic image and the at least one second endoscopic image into the deep convolutional network to perform training, to obtain the training parameter of the deep convolutional network.

In the embodiments of the present disclosure, the transformation performed by the server on the at least one first endoscopic image includes at least one of cropping, rotation, brightness jitter, color jitter, or contrast jitter. Such a transformation operation achieves a data enhancement effect. In an actual application, the quantity of transformations may be determined according to the quantity of alternative organ categories and/or the preset prediction precision.

For example, as shown in FIG. 3, in the input layer 301, 3011 represents the first endoscopic image acquired from the detection device. Two types of transformations are performed on 3011, including: a rotation transformation, to obtain a transformed second endoscopic image 3012; and a color transformation, to obtain a transformed second endoscopic image 3013. 3011, 3012 and 3013 are used as input images of the processing layer 302 to perform the feature extraction.

The training parameter obtained in step 203 and the deep convolutional network created in step 202 are used for a subsequent real-time prediction. In step 204, the server acquires a current endoscopic image of a to-be-examined user and predicts the current endoscopic image by using the deep convolutional network and based on a training parameter, to determine an organ category corresponding to the current endoscopic image. For example, the current endoscopic image inputted in the input layer 301 is predicted. For example, the current endoscopic image is classified as an "esophagus" category, or, the image is not a valid medical image and does not correspond to any organ, belonging to a "non-organ-image" category, so a doctor does not need to refer to the image when diagnosing a disease.

According to the foregoing exemplary embodiments, a training parameter of a deep convolutional network is determined according to at least one first endoscopic image and at least one second endoscopic image transformed from the at least one first endoscopic image. The transformed second endoscopic images may be used for classification training of the first endoscopic images. From the overall solution, the following technical effects can be obtained.

1) A feature extraction process is obtained completely by a model of a deep convolutional network through self-learning, while a researcher does not need to deeply understand a medical image, thus reducing the dependence on a professional level of a doctor, so that the whole prediction process is more intelligent.

2) The amount of annotated data used in a training process can be reduced, thus improving a training convergence speed, accelerating image classification, and improving resource utilization of a processing apparatus.

3) A training parameter is more accurate after iterations, and a classification result of a real-time prediction based on the training parameter is more accurate, providing clean and available data for next disease diagnosis.

4) Through such a deep convolutional network, not only low-level image features such as a color and a texture, but also more abstract semantic features, for example, whether a mucosa is smooth or not, whether there is a lot of wrinkles, can be extracted, which has strong robustness and can adapt to interferences caused by different angles and shooting methods used by different doctors in different hospitals for the same part.

5) After an accurate classification result is obtained, an available integration module for disease diagnosis of different organs can be provided. For example, for an esophagus organ, all endoscopic images belonging to an esophagus category after classification are used for screening and diagnosis of esophagus cancer. For a stomach organ, all endoscopic images belonging to a stomach category after classification are used for screening of diseases such as a gastritis and a stomach cancer.

In addition, when the deep convolutional network is created, at least one densely connected layer is added, which can maximize an information flow between all layers in the network, and reduce a problem of gradient dissipation in the training process to a certain extent. Moreover, because a large quantity of features are reused, a large quantity of features can be generated by using a small quantity of convolution kernels. A size of the final model is also relatively small, which reduces the quantity of parameters.

Figure 6:
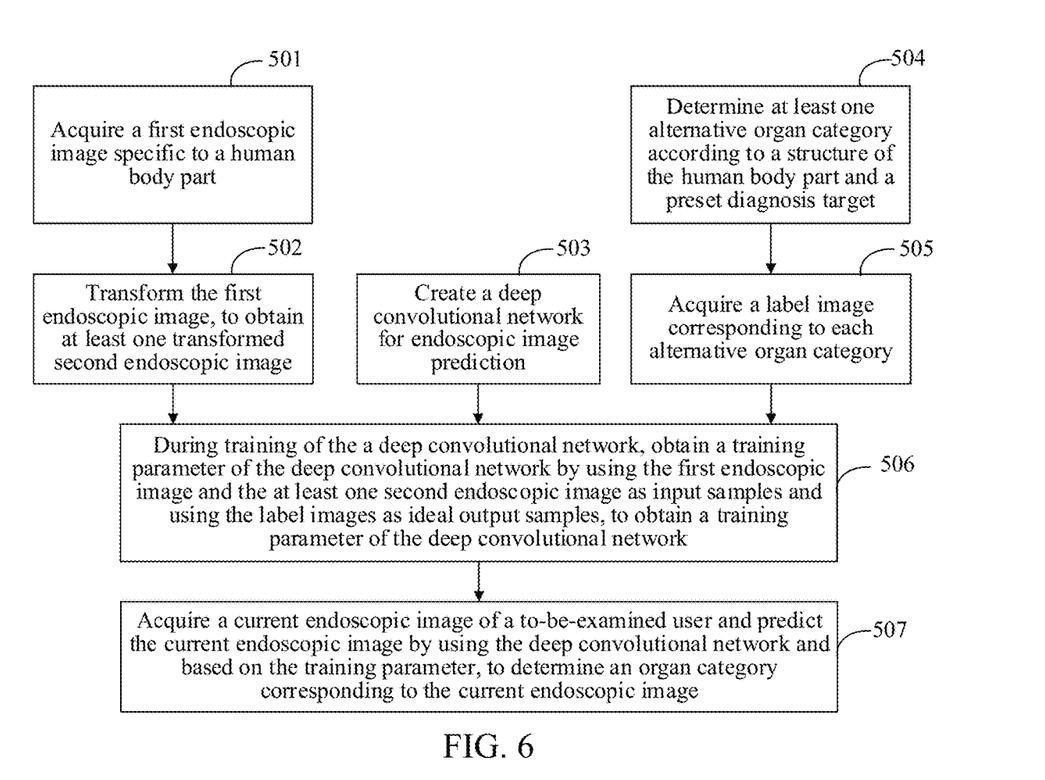
FIG. 6 is a schematic flowchart of an endoscopic image processing method according to another embodiment of the present disclosure.

FIG. 6 is a schematic flowchart of an endoscopic image processing method according to another embodiment of the present disclosure. As shown in FIG. 6, the following steps can be included.

In step 501, a server acquires at least one first endoscopic image specific to a human body part.

In step 502, the server transforms the at least one first endoscopic image, to obtain at least one second endoscopic image after transformation.

In step 503, the server creates a deep convolutional network for endoscopic image prediction.

For steps 501 to 503, refer to the description of the foregoing steps 201, 203, and 202, and details are not described herein again.

In step 504, the server determines at least one alternative organ category according to a structure of the human body part and a preset diagnosis target. In this step, the human body part may include a plurality of organs. During endoscopic image prediction by using the deep convolutional network, it is necessary to determine a plurality of alternative organ categories in advance. Specifically, when the human body part is divided, a plurality of regions may be defined according to the preset diagnosis target, and then the plurality of alternative organ categories may be determined. For example, stomach cancer and esophagus cancer are most common among malignant tumor types that occur frequently at present. If a diagnosis target is to diagnose the two organs, the alternative organ categories may be three categories: stomach, esophagus, and others.

Figure 7:
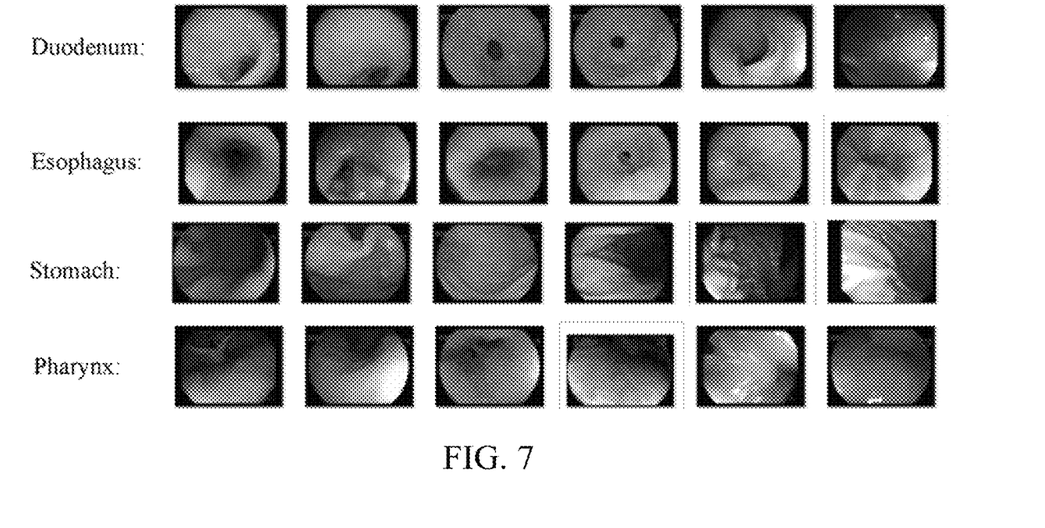
FIG. 7 is a schematic diagram of label images according to an embodiment of the present disclosure.

In step 505, the server acquires a label image corresponding to each alternative organ category. In this embodiment of the present disclosure, the label images may be acquired from a medical image database and annotated manually; alternatively, images with typical features of alternative organs may be filtered out from the collected first endoscopic images. FIG. 7 is a schematic diagram of label images according to an embodiment of the present disclosure. As shown in FIG. 7, a plurality of label images of a duodenum, an esophagus, a stomach, and an eye are provided respectively.

In step 506, during training of the deep convolutional network, the server perform straining by using the at least one first endoscopic image and the at least one second endoscopic image as input samples and using the label images as ideal output samples (namely, target output samples), to obtain a training parameter of the deep convolutional network. In this embodiment of the present disclosure, in a process of training the deep neural network, weight values are gradually adjusted iteratively according to the inputted image samples and the ideal output samples until convergence.

In step 507, the server acquires a current endoscopic image of a to-be-examined user and predicts the current endoscopic image by using the deep convolutional network and based on the training parameter, to determine an organ category corresponding to the current endoscopic image. The step is the same as step 204, and details are not described herein again.

Through the foregoing exemplary embodiment, considering that medical images of the same organ may be greatly different, alternative organ categories are properly designed, and distorted second endoscopic images obtained by transforming first endoscopic images are included in input samples, so that the quantity of label images can be greatly reduced, thereby resolving the problem of the limited quantity of label images as annotated data during training of a deep convolutional network.

Figure 8:
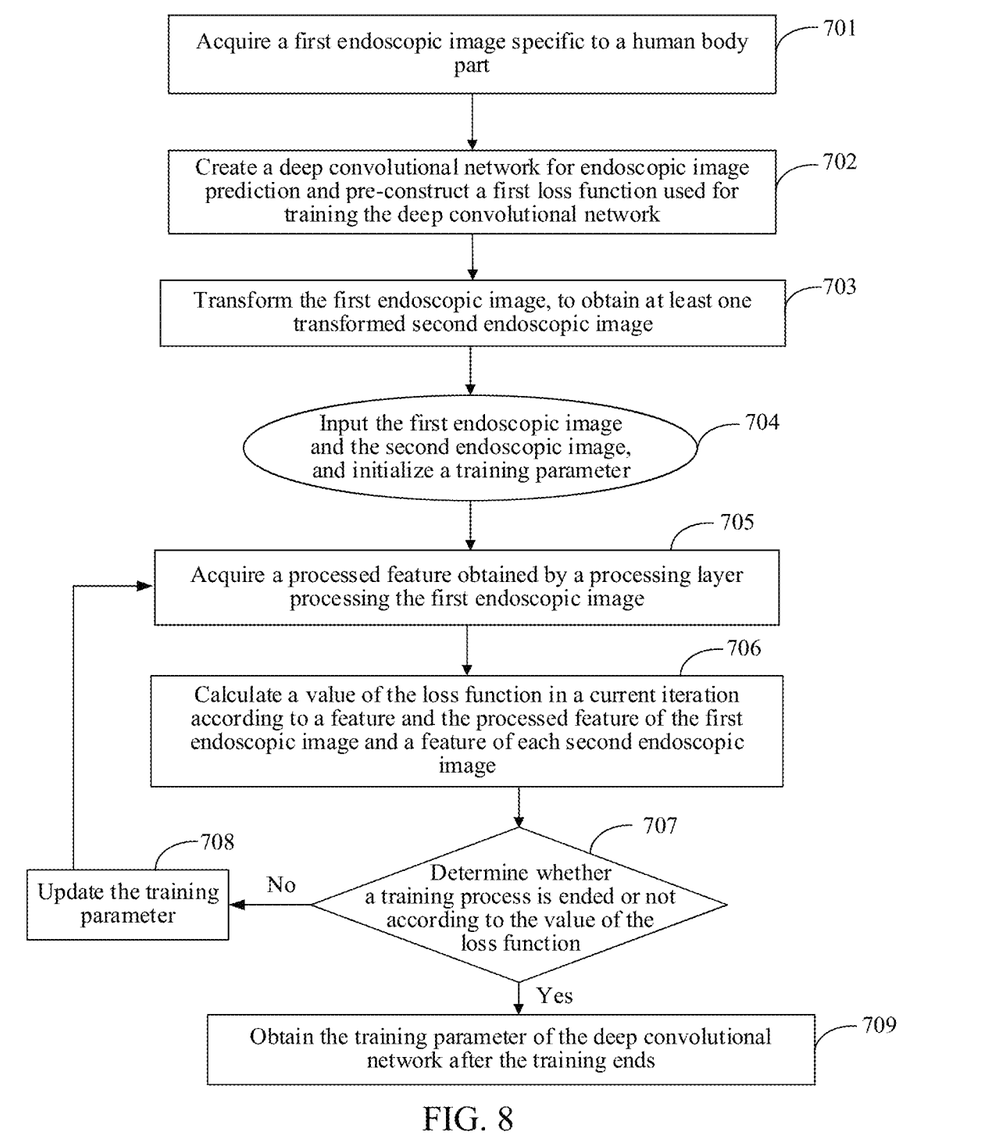
FIG. 8 is a schematic flowchart of training a deep convolutional network according to an embodiment of the present disclosure.

FIG. 8 is a schematic flowchart of training a deep convolutional network according to an embodiment of the present disclosure. As shown in FIG. 8, the following steps can be included.

In step 701, a server acquires at least one first endoscopic image specific to a human body part.

In step 703, the server transforms the at least one first endoscopic image, to obtain at least one transformed second endoscopic image.

In step 702, the server creates a deep convolutional network for endoscopic image prediction, the deep convolutional network including an input layer, a processing layer, and a classification layer.

During training of the deep convolutional network, a parameter may be adjusted by using back propagation iteratively until convergence. The back propagation may be divided into four different parts: forward transmission, loss function calculation, reverse transmission, and parameter update. In a process of the forward transmission, initial sample data, including the at least one first endoscopic image and the at least one transformed second endoscopic image, is inputted and transmitted in the processing layer. The loss function is constructed, helping the deep convolutional network update a training parameter until convergence.

In step 704, the server pre-constructs a loss function used for training the deep convolutional network. In this step, the loss function is constructed according to a preset convergence strategy.

In an embodiment of the present disclosure, specific to the inputted first endoscopic image and the transformed second endoscopic image, the convergence strategy is specifically a consistency constraint strategy, that is, features extracted by a model from transformations of the same endoscopic image are close to each other.

In another embodiment of the present disclosure, specific to the inputted first endoscopic image and a center feature of an organ category to which the first endoscopic image belongs, the convergence strategy is specifically a center aggregation strategy, that is, a distance between the first endoscopic images belonging to the same organ category is reduced, that is, an intra-class distance is reduced, and a distance between endoscopic images belonging to different organ categories is increased, that is, an inter-class distance is increased.

In step 704, the server inputs the at least one first endoscopic image and the at least one second endoscopic image, and initializes the deep convolutional network. In this step, the initialization of the deep convolutional network can include the following two initialization processes.

1) Initialize a training parameter w of the deep convolutional network, including weights of sub-layers in the processing layer and an output layer. For example, initial values of the training parameter are determined as random values [0.3, 0.1, 0.4, 0.2, 0.3 . . . ].

2) Initialize a center feature corresponding to the first endoscopic image. For example, an average value of label images of the categories is used as an initial value of the center feature.

At the beginning of training, the initialized training parameter and the center feature lead to a high value of the loss function. The objective of training the deep neural network is to make a predicted value the same as a real value. Therefore, the value of the loss function needs to be reduced to the greatest extent. A smaller loss value indicates that a prediction result is closer to the real value. In this process, the training parameter and center feature are adjusted iteratively, and the value of the loss function is calculated in each iteration, thereby minimizing a loss of the whole network.

During calculation of the loss function, the following steps 706 and 707 correspond to the foregoing consistency constraint strategy, and the following step 708 corresponds to the foregoing center aggregation strategy.

In step 705, the server acquires at least one processed feature obtained by the processing layer processing the at least one first endoscopic image.

In step 706, the server calculates a value of the loss function in a current iteration according to the at least one processed feature and a feature of the at least one second endoscopic image.

The foregoing consistency constraint strategy is as follows: in the loss function, a plurality of first distances between the processed features of the first endoscopic images and the features of the second endoscopic images are calculated respectively, and consistency between the first endoscopic images and the second endoscopic images is constrained by the plurality of first distances.

Specifically, if the training parameter is w, an eigenvector of an $i^{th}$ first endoscopic image is $x_i$, and an eigenvector of an $i^{th}$ label image is $y_i$, the loss function L(w) may be calculated iteratively according to the following formula:

$$L(w) = -\frac{1}{n}\sum_{i=1}^{n}\left(y_i \log f(x_i; w) - \frac{r}{2}\sum_{k=1}^{m}\|h_0 - h_k\|_2^2\right) + \frac{\lambda}{2}\|w\|_2^2 \quad (2)$$

where n is the quantity of the inputted first endoscopic images, and m is the quantity of the second endoscopic images obtained by transforming the first endoscopic images. Further, $y_i \log f(x_i; w)$ represents a cross-entropy loss of classification.

$$\frac{\lambda}{2}\|w\|_2^2$$

represents an L2 regularization parameter. The variable $h_0$ is an eigenvector outputted by the processing layer according to the first endoscopic image, that is, a processed eigenvector. $h_k$ is an eigenvector of a $k^{th}$ second endoscopic image. Additionally, r and λ are hyper parameters, both of which are values greater than 0.

In addition, i is an integer greater than or equal to 1 and less than or equal to n, and k is an integer greater than or equal to 1 and less than or equal to m.

It can be seen that in the foregoing formula (2) that, the first distance is $h_0 - h_k$, and the expression $$\frac{r}{2}\sum_{k=1}^{m}\|h_0 - h_k\|_2^2$$

reflects the consistency constraint between the endoscopic images before and after the transformation.

In an example, the server calculates a plurality of second distances between features of the first endoscopic images and center features corresponding to the first endoscopic images. If it is defined that the center feature corresponding to the first endoscopic image is $c_{y_i}$, and the center feature is $L_C$, then the second distance is $x_i - c_{y_i}$, representing a center loss.

In step 709 an example, the server calculates the value of the loss function according to the plurality of first distances and the plurality of second distances. In a case that only the consistency constraint is considered, the value of loss function may be obtained through calculation according to the foregoing formula (2).

When the consistency constraint and the center aggregation strategy are considered, the loss function is calculated according to the first distance and the second distance. The specific calculation is $$L(w) = -\frac{1}{n}\sum_{i=1}^{n}\left(y_i \log f(x_i; w) - \frac{r}{2}\sum_{k=1}^{m}\|h_0 - h_k\|_2^2\right) + \frac{\lambda}{2}\|w\|_2^2 + L_C \quad (3)$$

where, $$L_C = \frac{1}{2}\sum_{i=1}^{n}\|x_i - c_{y_i}\|_2^2 \quad (4)$$

In step 707, the server determines whether a training process is ended or not according to the value of the loss function. If yes, step 709 is performed; otherwise, steps 708 is performed.

In a process of successive iterations, the loss function is minimized, that is, minL (w). Whether to stop the iteration can be determined by determining whether the value of the loss function reaches an acceptable threshold. After the iteration stops, the whole training process is ended.

In step 708, the server updates a training parameter. Then, step 706 is further performed to perform the next iteration process.

In step 712, the server updates the center feature. Then, step 708 is further performed to perform the next iteration process.

In step 713, the server obtains the training parameter of the deep convolutional network after the training ends.

Through the foregoing exemplary embodiment, a loss function used for training a deep convolutional network is pre-constructed. A value of the loss function of each iteration is calculated according to processed features of first endoscopic images and a feature of each second endoscopic image. A consistency constraint is introduced, so that a more stable feature can be preferentially found and a convergence speed of a training process can be accelerated, until an optimal solution is obtained. In addition, a center aggregation strategy is considered in the loss function, to ensure that features learned by a model for each category is more stable and cohesive, thereby further improving a generalization ability of the model in a real environment.

Figure 9:
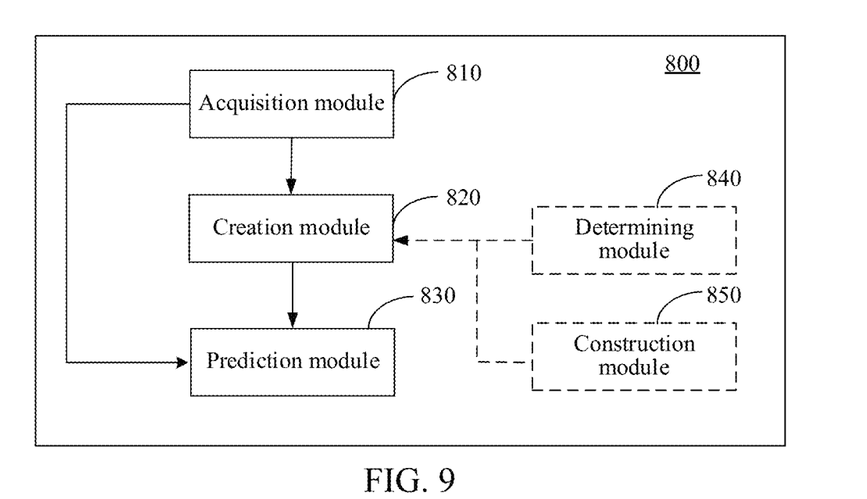
FIG. 9 is a schematic structural diagram of an endoscopic image processing apparatus according to an embodiment of the present disclosure.

FIG. 9 is a schematic structural diagram of an endoscopic image processing apparatus according to an embodiment of the present disclosure. As shown in FIG. 9, an apparatus 800 can include an acquisition module 810 that is configured to acquire a first endoscopic image specific to a human body part through a detection device including an endoscope, and acquire a current endoscopic image of a to-be-examined user. The apparatus 800 can further include a creation module 820 that is configured to create a deep convolutional network for endoscopic image prediction, and determine a training parameter of the deep convolutional network according to the at least one first endoscopic image acquired by the acquisition module 810 and at least one second endoscopic image transformed from the first endoscopic image. Additionally, the apparatus can include a prediction module 830 that is configured to predict the current endoscopic image by using the deep convolutional network created by the creation module 820 and based on the training parameter, to determine an organ category corresponding to the current endoscopic image.

Of course, it should be understood that one or more of the modules described in embodiments of this disclosure can be implemented, for example, by processing circuitry.

In an exemplary embodiment of the present disclosure, the apparatus 800 further can further include a determining module 840 that is configured to determine at least one alternative organ category according to a structure of the human body part and a preset diagnosis target, and acquire a label image corresponding to each alternative organ category. Also, the creation module 820 can be configured to perform training by using the first endoscopic image and the at least one second endoscopic image as input samples and using the label images determined by the determining module 840 as ideal output samples, to obtain the training parameter.

In an embodiment of the present disclosure, the deep convolutional network includes an input layer, a processing layer, and a classification layer. The creation module 820 is configured to add at least one densely connected layer into the processing layer, the densely connected layer including a plurality of connected sub-layers. For each connected sub-layers, a feature outputted by other connected sub-layers before the connected sub-layer is used as an input of the connected sub-layer.

In an embodiment of the present disclosure, the creation module 820 is configured to add a transition layer between two adjacent densely connected layers, and set a value of a feature compression ratio of the transition layer according to a preset prediction precision.

In an embodiment of the present disclosure, the deep convolutional network includes an input layer, a processing layer, and a classification layer. The apparatus 800 can further include a construction module 850 that is configured to pre-construct a loss function used for training the deep convolutional network. The creation module 820 can be configured to perform the following processing iteratively during training of the deep convolutional network, including acquiring at least one processed feature obtained by the processing layer processing the at least one first endoscopic image; calculating a value of the loss function in a current iteration according to the processed feature and a feature of each second endoscopic image; and determining whether a training process is ended or not according to the value of the loss function, where the training parameter is obtained in response to determining that the training process is ended.

In an embodiment of the present disclosure, the creation module 820 is further configured to initialize a center feature of an organ category to which the at least one first endoscopic image belongs, calculate first distances between the processed features and the features of the second endoscopic images, calculate second distances between features of the first endoscopic images and the center features corresponding to the first endoscopic images, and calculate the value according to the first distances and the second distances.

In an embodiment of the present disclosure, the transformation performed on the first endoscopic image includes at least one of cropping, rotation, brightness jitter, color jitter, or contrast jitter.

Figure 10:
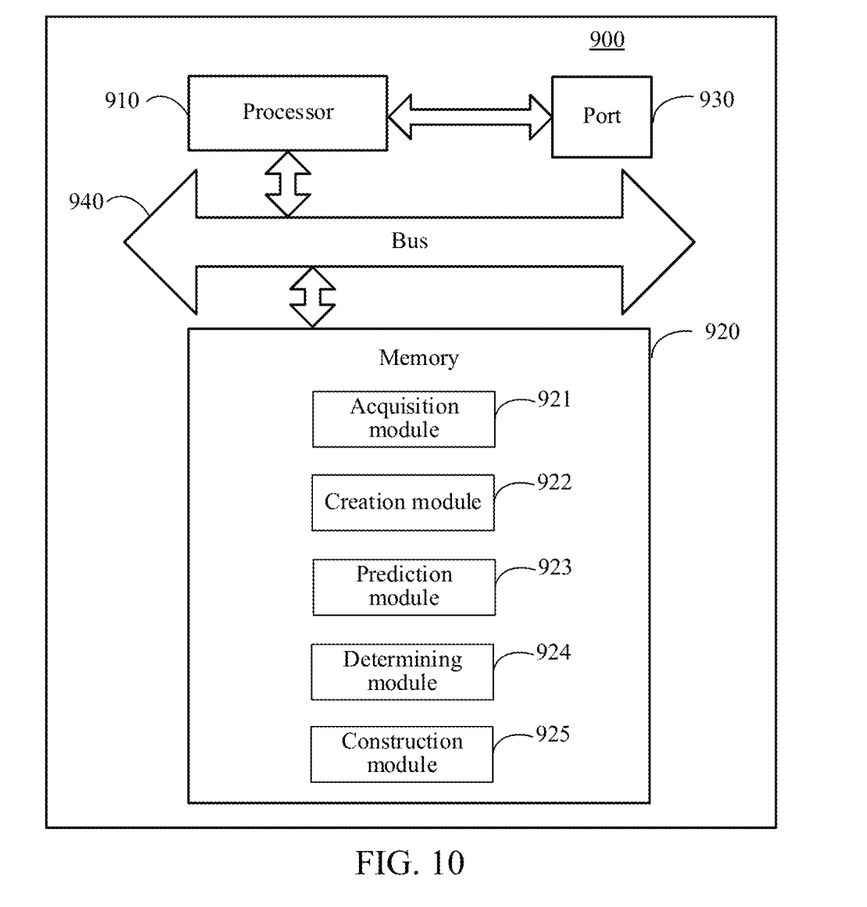
FIG. 10 is a schematic structural diagram of an endoscopic image processing apparatus according to another embodiment of the present disclosure.

FIG. 10 is a schematic structural diagram of an endoscopic image processing apparatus according to another embodiment of the present disclosure. As shown in FIG. 10, an apparatus 900 can include a processor 910, a memory 920, a port 930, and a bus 940. The processor 910 and the memory 920 are interconnected by using the bus 940. The processor 910 may receive and send data by using the port 930.

The processor 910 is configured to execute machine readable instruction modules stored in the memory 920. The memory 920 stores the non-transitory machine readable instruction modules executable by the processor 910. The instruction modules executable by the processor 910 can include an acquisition module 921, a creation module 922, and a prediction module 923, that, when executed by the processor 910, the acquisition module 921 may be configured to acquire a first endoscopic image specific to a human body part through a detection device including an endoscope, and acquire a current endoscopic image of a to-be-examined user. Further, when the instruction modules are executed by the processor 910, the creation module 922 may be configured to create a deep convolutional network for endoscopic image prediction, and determine a training parameter of the deep convolutional network according to the at least one first endoscopic image acquired by the acquisition module 921 and at least one second endoscopic image transformed from the first endoscopic image. Further, when the instruction modules are executed by the processor 910, the prediction module 923 may be configured to predict the current endoscopic image by using the deep convolutional network created by the creation module 922 and based on the training parameter, to determine an organ category corresponding to the current endoscopic image.

In an embodiment of the present disclosure, the instruction modules executable by the processor 910 can further include a determining module 924. When the instructions are executed by the processor 910, the determining module 924 may be configured to determine at least one alternative organ category according to a structure of the human body part and a preset diagnosis target, and acquire a label image corresponding to each alternative organ category before training the deep convolutional network. Further, when the instructions are executed by the processor 910, the creation module 922 may be configured perform training by using the at least one first endoscopic image and the at least one second endoscopic image as input samples and using the label images determined by the determining module 924 as ideal output samples, to obtain the training parameter.

In an embodiment of the present disclosure, the instruction modules executable by the processor 910 further include a construction module 925. When the instruction modules are executed by the processor 910, the construction module 925 may be configured to pre-construct a loss function used for training the deep convolutional network. Further, when the instruction modules are executed by the processor 910, the creation module 922 may be configured to perform the following processing iteratively during training of the deep convolutional network: acquiring at least one processed feature obtained by a processing layer processing the at least one first endoscopic image; calculating a value of the loss function in a current iteration according to the processed feature and a feature of each second endoscopic image; and determining whether a training process is ended or not according to the value of the loss function, where the training parameter is obtained in response to determining that the training process is ended.

It can be learned from above that when the instruction modules stored in the memory 920 are executed by the processor 910, various functions of the acquisition module, the creation module, the prediction module, the determining module, and the construction module in the foregoing embodiments may be implemented.

In the foregoing apparatus embodiment, specific methods for implementing respective functions by each module and unit are all described in the method embodiments, and details are not described herein again. In addition, the functional modules in the embodiments of the present disclosure may be integrated into one processing unit, or each of the modules may exist alone physically, or two or more modules are integrated into one unit. The integrated unit may be implemented in the form of hardware, or may be implemented in the form of a software functional unit.

In an embodiment, an endoscopic image processing system is provided, including a human body detection device and an endoscopic image processing apparatus, the human body detection device being configured to detect a human body part, and transmit at least one detected first endoscopic image to the endoscopic image processing apparatus. Further, the endoscopic image processing apparatus being configured to acquire the at least one first endoscopic image from the human body detection device, create a deep convolutional network for endoscopic image prediction and determine a training parameter of the deep convolutional network according to the at least one first endoscopic image and at least one second endoscopic image transformed from the at least one first endoscopic image, and acquire a current endoscopic image of a to-be-examined user, and predict the current endoscopic image by using the deep convolutional network and based on the training parameter, to determine an organ category corresponding to the current endoscopic image.

In an embodiment, the endoscopic image processing apparatus is further configured to determine at least one alternative organ category according to a structure of the human body part and a preset diagnosis target, acquire a label image corresponding to each alternative organ category; perform training by using the at least one first endoscopic image and the at least one second endoscopic image as input samples and using the label images as target output samples, to obtain the training parameter.

In an embodiment, the deep convolutional network includes an input layer, a processing layer and a classification layer, and the endoscopic image processing apparatus is further configured to pre-construct a loss function used for training the deep convolutional network, perform the following processing iteratively during training of the deep convolutional network: acquiring at least one processed feature obtained by the processing layer processing the at least one first endoscopic image, calculating a value of the loss function in a current iteration according to the at least one processed feature and a feature of the at least one second endoscopic image, and determining whether a training process is ended or not according to the value of the loss function, where the training parameter is obtained in response to determining that the training process is ended.

In an embodiment, during training of the deep convolutional network, the endoscopic image processing apparatus is further configured to initialize a center feature of an organ category to which the at least one first endoscopic image belongs, calculate a plurality of first distances between the processed features and the features of the second endoscopic images, calculate a plurality of second distances between features of the first endoscopic images and the center features corresponding to the first endoscopic images, and calculate the value of the loss function according to the plurality of first distances and the plurality of second distances.

In an embodiment, a computer device is provided, including at least one processor and at least one memory, the at least one memory storing at least one piece of program code, and the at least one piece of program code being loaded and executed by the at least one processor to implement the steps of acquiring a current endoscopic image of a to-be-examined user, predicting the current endoscopic image by using a deep convolutional network based on a training parameter, the training parameter being determined according to at least one first endoscopic image and at least one second endoscopic image transformed from the at least one first endoscopic image, the at least one first endoscopic image corresponding to a human body part, and determining an organ category corresponding to the current endoscopic image.

In an embodiment, the at least one processor can be configured to perform the steps of acquiring the at least one first endoscopic image specific to the human body part, and creating the deep convolutional network for endoscopic image prediction, determining the training parameter of the deep convolutional network according to the at least one first endoscopic image and the at least one second endoscopic image transformed from the at least one first endoscopic image.

In an embodiment, the at least one processor is configured to perform the steps of determining at least one alternative organ category according to a structure of the human body part and a preset diagnosis target, and acquiring a label image corresponding to each alternative organ category. Further the at least one processor can be configured to perform the steps of performing training by using the at least one first endoscopic image and the at least one second endoscopic image as input samples and using the label images as target output samples, to obtain the training parameter.

In an embodiment, the deep convolutional network includes an input layer, a processing layer and a classification layer, and the at least one processor is configured to perform the steps of adding at least one densely connected layer into the processing layer, the densely connected layer including a plurality of connected sub-layers, and, for each connected sub-layer, using a feature outputted by other connected sub-layers before the connected sub-layer as an input of the connected sub-layer.

In an embodiment, the at least one processor is configured to perform the step of adding a transition layer between two adjacent densely connected layers, and setting a feature compression ratio of the transition layer according to a preset prediction precision.

In an embodiment, the deep convolutional network includes an input layer, a processing layer and a classification layer, and the at least one processor is configured to perform the steps of pre-constructing a loss function used for training the deep convolutional network, performing the following processing iteratively during training of the deep convolutional network, acquiring at least one processed feature obtained by the processing layer processing the at least one first endoscopic image, calculating a value of the loss function in a current iteration according to the at least one processed feature and a feature of the at least one second endoscopic image, and determining whether a training process is ended or not according to the value of the loss function, where the training parameter is obtained in response to determining that the training process is ended.

In an embodiment, during training of the deep convolutional network, the at least one processor is configured to perform the steps of initializing a center feature of an organ category to which the at least one first endoscopic image belongs, calculating a plurality of first distances between the processed features and the features of the second endoscopic images, calculating a plurality of second distances between features of the first endoscopic images and the center features corresponding to the first endoscopic images, and calculating the value of the loss function according to the plurality of first distances and the plurality of second distances.

In an embodiment, the transformation performed on the at least one first endoscopic image includes at least one of cropping, rotation, brightness jitter, color jitter, or contrast jitter. In addition, each embodiment of the present disclosure may be implemented by a data processing program that is executed by a data processing device such as a computer. Apparently, a data processing program constitutes the present disclosure. In addition, generally, a data processing program stored in a storage medium is directly read from the storage medium for execution or the program is installed on or replicated to a storage device (such as a hard disk or memory) of a data processing device for execution. Therefore, such a storage medium also constitutes the present disclosure. The storage medium may use any type of recording manner, such as a paper storage medium (such as a paper tape), a magnetic storage medium (such as a floppy disk, a hard disk, or a flash memory), an optical storage medium (such as a CD-ROM), or a magneto-optical storage medium (such as an MO). Therefore, the present disclosure further discloses a storage medium, storing a data processing program, the data processing program being used for performing any one of the embodiments of the foregoing methods in the present disclosure.

In some embodiments, the storage medium may be a computer readable storage medium, storing computer readable instructions, the computer readable instructions, when executed by at least one processor, causing the at least one processor to load and perform the steps of acquiring a current endoscopic image of a to-be-examined user, predicting the current endoscopic image by using a deep convolutional network based on a training parameter, the training parameter being determined according to at least one first endoscopic image and at least one second endoscopic image transformed from the at least one first endoscopic image, the at least one first endoscopic image corresponding to a human body part, and determining an organ category corresponding to the current endoscopic image.

In an embodiment, the at least one processor is configured to perform the steps of acquiring the at least one first endoscopic image specific to the human body part, and creating the deep convolutional network for endoscopic image prediction, determining the training parameter of the deep convolutional network according to the at least one first endoscopic image and the at least one second endoscopic image transformed from the at least one first endoscopic image.

In an embodiment, the at least one processor is configured to perform the steps of determining at least one alternative organ category according to a structure of the human body part and a preset diagnosis target, acquiring a label image corresponding to each alternative organ category, and performing training by using the at least one first endoscopic image and the at least one second endoscopic image as input samples and using the label images as target output samples, to obtain the training parameter.

In an embodiment, the deep convolutional network includes an input layer, a processing layer and a classification layer, and the at least one processor is configured to perform the steps of adding at least one densely connected layer into the processing layer, the densely connected layer including a plurality of connected sub-layers, and, for each connected sub-layer, using a feature outputted by other connected sub-layers before the connected sub-layer as an input of the connected sub-layer.

In an embodiment, the at least one processor is configured to perform the step of adding a transition layer between two adjacent densely connected layers, and setting a feature compression ratio of the transition layer according to a preset prediction precision.

In an embodiment, the deep convolutional network includes an input layer, a processing layer and a classification layer, and the at least one processor is configured to perform the step of pre-constructing a loss function used for training the deep convolutional network, performing the following processing iteratively during training of the deep convolutional network, acquiring at least one processed feature obtained by the processing layer processing the at least one first endoscopic image, calculating a value of the loss function in a current iteration according to the at least one processed feature and a feature of the at least one second endoscopic image, and determining whether a training process is ended or not according to the value of the loss function, where the training parameter is obtained in response to determining that the training process is ended.

In an embodiment, during training of the deep convolutional network, the at least one processor is configured to perform the steps of initializing a center feature of an organ category to which the at least one first endoscopic image belongs, calculating a plurality of first distances between the processed features and the features of the second endoscopic images, calculating a plurality of second distances between features of the first endoscopic images and the center features corresponding to the first endoscopic images, and calculating the value of the loss function according to the plurality of first distances and the plurality of second distances.

In an embodiment, the transformation performed on the at least one first endoscopic image includes at least one of cropping, rotation, brightness jitter, color jitter, or contrast jitter.

The foregoing descriptions are merely exemplary embodiments of the present disclosure, but are not intended to limit the present disclosure. Any modification, equivalent replacement, or improvement made without departing from the spirit and principle of the present disclosure is to be fall within the protection scope of the present disclosure.

What is claimed is:

1. An endoscopic image processing method, comprising:
receiving at least one first endoscopic image specific to a human body part;
creating a deep convolutional network for endoscopic image prediction;
determining a training parameter of the deep convolutional network according to both (i) the at least one first endoscopic image and (ii) at least one second endoscopic image transformed from the at least one first endoscopic image, the determining the training parameter includes iteratively adjusting the training parameter according to a loss function of the deep convolutional network, a value of the loss function being determined based on a feature of the at least one first endoscopic image and a feature of the at least one second endoscopic image;
receiving a current endoscopic image of a to-be-examined user;
predicting the current endoscopic image by using the deep convolutional network based on the training parameter that is determined according to the at least one first endoscopic image and the at least one second endoscopic image transformed from the at least one first endoscopic image, where the at least one first endoscopic image corresponds to the human body part; and
determining an organ category corresponding to the current endoscopic image.

2. The method according to claim 1, further comprising:
determining at least one alternative organ category according to a structure of the human body part and a preset diagnosis target;
acquiring a label image corresponding to each alternative organ category;
wherein the determining the training parameter of the deep convolutional network according to the at least one first endoscopic image and the at least one second endoscopic image transformed from the at least one first endoscopic image further comprises:
performing training by using the at least one first endoscopic image and the at least one second endoscopic image as input samples, and using the label images as target output samples in order to obtain the training parameter.

3. The method according to claim 1, wherein the deep convolutional network includes an input layer, a processing layer, and a classification layer, and the creating the deep convolutional network for the endoscopic image prediction further comprises:
adding at least one densely connected layer into the processing layer, the densely connected layer including a plurality of connected sub-layers; and
using a feature outputted by other connected sub-layers before the connected sub-layer as an input of the connected sub-layer for each connected sub-layer.

4. The method according to claim 3, wherein the adding at least one densely connected layer into the processing layer further comprises:
adding a transition layer between two adjacent densely connected layers; and
setting a feature compression ratio of the transition layer according to a preset prediction precision.

5. The method according to claim 1, wherein the deep convolutional network includes an input layer, a processing layer, and a classification layer, and the method further comprises:
pre-constructing the loss function used for training the deep convolutional network, and
wherein the determining the training parameter of the deep convolutional network according to the at least one first endoscopic image and the at least one second endoscopic image transformed from the at least one first endoscopic image further comprises iteratively performing a processing during training of the deep convolutional network that includes:
acquiring at least one processed feature obtained by the processing layer processing the at least one first endoscopic image;
calculating a value of the loss function in a current iteration according to the at least one processed feature and a feature of the at least one second endoscopic image; and
determining whether a training process is ended based on the value of the loss function, wherein the training parameter is obtained in response to determining that the training process is ended.

6. The method according to claim 5, wherein during training of the deep convolutional network, the method further comprises:
initializing a center feature of the organ category to which the at least one first endoscopic image belongs, and
wherein the calculating the value of the loss function in the current iteration according to the at least one processed feature and the feature of the at least one second endoscopic image further comprises:
calculating a plurality of first distances between the processed features and the features of the second endoscopic images;
calculating a plurality of second distances between features of the first endoscopic images and the center features corresponding to the first endoscopic images; and
calculating the value of the loss function according to the plurality of first distances and the plurality of second distances.

7. The method according to claim 1, wherein the transformation performed on the at least one first endoscopic image comprises at least one of cropping, rotation, brightness jitter, color jitter, or contrast jitter.

8. An endoscopic image processing system comprising:
an imaging device including an imaging sensor that is configured to capture at least one first endoscopic image specific to a human body part; and
an endoscopic image processing apparatus, including processing circuitry that is configured to:
receive the at least one first endoscopic image from the imaging device,
create a deep convolutional network for endoscopic image prediction,
determine a training parameter of the deep convolutional network according to both (i) the at least one first endoscopic image and (ii) at least one second endoscopic image that is transformed from the at least one first endoscopic image, the determination of the training parameter includes iteratively adjusting the training parameter according to a loss function of the deep convolutional network, a value of the loss function being determined based on a feature of the at least one first endoscopic image and a feature of the at least one second endoscopic image; and
receive a current endoscopic image of a to-be-examined user,
predict the current endoscopic image by using the deep convolutional network based on the training parameter that is determined according to the at least one first endoscopic image and the at least one second endoscopic image transformed from the at least one first endoscopic image, and
determine an organ category corresponding to the current endoscopic image.

9. The system according to claim 8, wherein the processing circuitry is further configured to:
determine at least one alternative organ category according to a structure of the human body part and a preset diagnosis target;
acquire a label image corresponding to each alternative organ category; and
perform training by using the at least one first endoscopic image and the at least one second endoscopic image as input samples and using the label images as target output samples to obtain the training parameter.

10. The system according to claim 8, wherein the deep convolutional network further includes an input layer, a processing layer, and a classification layer, and the processing circuitry is further configured to:
pre-construct the loss function used for training the deep convolutional network; and
iteratively perform a process during training of the deep convolutional network including:
acquire at least one processed feature obtained by the processing layer processing the at least one first endoscopic image;
calculate a value of the loss function in a current iteration according to the at least one processed feature and a feature of the at least one second endoscopic image; and
determine whether a training process is ended based on the value of the loss function, wherein the training parameter is obtained in response to determining that the training process is ended.

11. The system according to claim 10, wherein the processing circuitry is further configured to:
initialize a center feature of the organ category to which the at least one first endoscopic image belongs;

calculate a plurality of first distances between the processed features and the features of the second endoscopic images;
calculate a plurality of second distances between features of the first endoscopic images and the center features corresponding to the first endoscopic images; and
calculate the value of the loss function according to the plurality of first distances and the plurality of second distances.

12. An information processing apparatus, comprising:
processing circuitry configured to:
acquire at least one first endoscopic image specific to a human body part;
create a deep convolutional network for endoscopic image prediction;
determine a training parameter of the deep convolutional network according to both (i) the at least one first endoscopic image and (ii) at least one second endoscopic image transformed from the at least one first endoscopic image, the determination of the training parameter includes iteratively adjusting the training parameter according to a loss function of the deep convolutional network, a value of the loss function being determined based on a feature of the at least one first endoscopic image and a feature of the at least one second endoscopic image;
receive a current endoscopic image of a to-be-examined user;
predict the current endoscopic image by using the deep convolutional network based on the training parameter that is determined according to the at least one first endoscopic image and the at least one second endoscopic image transformed from the at least one first endoscopic image, where the at least one first endoscopic image corresponds to the human body part; and
determine an organ category corresponding to the current endoscopic image.

13. The information processing apparatus according to claim 12, wherein the processing circuitry is configured to:
determine at least one alternative organ category according to a structure of the human body part and a preset diagnosis target;
acquire a label image corresponding to each alternative organ category; and
perform training by using the at least one first endoscopic image and the at least one second endoscopic image as input samples and using the label images as target output samples to obtain the training parameter.

14. The information processing apparatus according to claim 12, wherein the deep convolutional network includes an input layer, a processing layer and a classification layer, and the processing circuitry is configured to:

add at least one densely connected layer into the processing layer, where the densely connected layer includes a plurality of connected sub-layers; and
use a feature outputted by other connected sub-layers before the connected sub-layer as an input of the connected sub-layer for each connected sub-layer.

15. The information processing apparatus according to claim 14, wherein the processing circuitry is configured to:
add a transition layer between two adjacent densely connected layers; and
set a feature compression ratio of the transition layer according to a preset prediction precision.

16. The information processing apparatus according to claim 13, wherein the deep convolutional network includes an input layer, a processing layer, and a classification layer, and the processing circuitry is configured to:
a pre-construct the loss function used for training the deep convolutional network; and
perform an iterative process during training of the deep convolutional network that includes:
acquire at least one processed feature obtained by the processing layer processing the at least one first endoscopic image;
a value of the loss function in a current iteration according to the at least one processed feature and a feature of the at least one second endoscopic image; and
whether a training process is ended according to the value of the loss function, wherein the training parameter is obtained in response to determining that the training process is ended.

17. The information processing apparatus according to claim 16, wherein, during training of the deep convolutional network, the processing circuitry is configured to:
initialize a center feature of the organ category to which the at least one first endoscopic image belongs;
calculate a plurality of first distances between the processed features and the features of the second endoscopic images;
calculate a plurality of second distances between features of the first endoscopic images and the center features corresponding to the first endoscopic images; and
calculate the value of the loss function according to the plurality of first distances and the plurality of second distances.

18. The information processing apparatus according to claim 12, wherein the transformation performed on the at least one first endoscopic image includes at least one of cropping, rotation, brightness jitter, color jitter, or contrast jitter.

* * * * *